United States Patent [19]

Soldner

[11] 4,163,394

[45] Aug. 7, 1979

[54] METHOD OF ULTRASONIC SCANNING OF BODIES

[75] Inventor: Richard E. Soldner, Erlangen, Fed. Rep. of Germany

[73] Assignee: Siemens Aktiengesellschaft, Berlin & Munich, Fed. Rep. of Germany

[21] Appl. No.: 694,608

[22] Filed: Jun. 10, 1976

[30] Foreign Application Priority Data

Jun. 30, 1975 [DE] Fed. Rep. of Germany ....... 2529112

[51] Int. Cl.² ............................................. A61B 10/00
[52] U.S. Cl. ..................................... 73/626; 128/1 R; 128/660
[58] Field of Search ................ 128/2 V, 2.05 Z, 1 R; 73/71.5 US, 67.8 S, 625, 626, 642, 641

[56] References Cited

U.S. PATENT DOCUMENTS

| | | | |
|---|---|---|---|
| 2,728,869 | 12/1955 | Pohlman | 310/8.7 |
| 3,269,173 | 8/1966 | von Ardenne | 128/2 V X |
| 3,938,371 | 2/1976 | Dini | 73/67.8 S |
| 3,990,300 | 11/1976 | Kossoff | 73/67.8 S |

FOREIGN PATENT DOCUMENTS

| | | | |
|---|---|---|---|
| 704633 | 2/1954 | United Kingdom | 128/2 V |
| 184000 | 7/1966 | U.S.S.R. | 128/2 V |

OTHER PUBLICATIONS

Kossoff et al., "Journal of the Acoustical Society of Amer.," vol. 44, No. 5, 1968, pp. 1310–1318.

*Primary Examiner*—Robert W. Michell
*Assistant Examiner*—Michael H. Thaler
*Attorney, Agent, or Firm*—Hill, Van Santen, Steadman, Chiara & Simpson

[57] ABSTRACT

In the illustrated embodiment, ultrasonic transmitter/receiver elements are arranged along a curved formation within a housing containing a coupling medium which is a good conductor of ultrasonic energy (for example a water medium) and are successively excited to direct ultrasonic beam energy via the coupling medium to an ultrasonic window of the housing. The transducer elements are mounted at different angular orientations such that their beam paths converge external to the ultrasonic window. The curvature of a carrier for the transducer elements may be controlled to adjust the distance of the point of convergence beyond the window without changing the length of the acoustic path in the coupling medium, or the transducer elements and/or ultrasonic window may be bodily shifted to simultaneously change the length of the acoustic path and the distance of the convergence point beyond the window. Internal body regions accessible through narrow acoustic apertures at varying depths dependent on individual body characteristics may thus be reached for scanning by appropriate adjustment of the depth of the convergence point of the ultrasonic beam paths, the diverging beam paths beyond such depth providing for a sector scanning configuration within the desired body region.

2 Claims, 2 Drawing Figures

METHOD OF ULTRASONIC SCANNING OF BODIES

BACKGROUND OF THE INVENTION

The invention concerns an ultrasonic applicator for ultrasonic scanning of internal body regions, particularly for the purpose of obtaining ultrasonic echo sectional views, with an ultrasonic transmitting/receiving system consisting of a plurality of ultrasonic transmitter/receiver elements, which are arranged adjacent one another and which can be activated in chronological succession.

An ultrasonic applicator of this type is prior art, wherein the individual ultrasonic transmitter/receiver elements are arranged next to one another in one plane. During chronologically successive excitation of the individual transmitter/receiver elements, the ultrasonic beam energy in the body area which is to be examined is shifted parallel to itself. Thus, the ultrasonic beam energy scans a body area along a succession of mutually parallel lines. During the corresponding linear imaging of the ultrasonic echo signals received from each of the scanning lines, on the viewing screen of an oscilloscope, a sectional view of the body region which is to be examined is obtained in the scanning plane.

Particularly in medical ultrasonic diagnosis, however, there are body regions of interest which are accessible from the body surface only through relatively narrow acoustical apertures, such as, for example, in the case of heart examinations, the intermediary spaces between the ribs, or, in the case of skull examinations, thin bone areas at specific locations at the top of the skull (calvarium); for example, the thin bone area above the ear. Ultrasonic scanning procedures which function according to the principle of sector scanning would be advantageous for the scanning of such body regions.

SUMMARY OF THE INVENTION

Accordingly, it is an object of the present invention to provide an ultrasonic applicator of the general type initially mentioned, but so constructed that it permits of a sector scanning. The inventive ultrasonic applicator is to be such that a direct coupling of the cyclically scanning sound head on the body surface is avoided. Aside from the fact that direct coupling of a cyclically scanning sound head on the body surface, of a patient, for example, is not without problems, and moreover, that the vibration of an ultrasonic generator on the skin surface may annoy the patient, the usual disturbances occurring in connection with a direct coupling of a sound head are present. Such disturbances include, for example, the problem of multiple echos, which occur between strongly reflective boundary surfaces of the body and the sound head application surface, and which, as superimposed points of light in the ultrasonic echo sectional view, make difficult the diagnostic evaluation of the sectional view. In addition, ambiguities due to minor lobes may also result, and there is the disadvantage of dead zones in the coupling area, since the direct coupling of a strong transmission pulse prevents an echo reading from this close range. An additional disturbing disadvantage would result in the case of a directly coupled sector scanning field, since the origin of the divergent scanning lines would be in front of, or on, the body surface, respectively. If the access aperture for acoustical energy is located in the interior of the body, such as, for example, in the space between the ribs, which under certain circumstances may lie within the body at a depth of up to several centimeters, the potential advantage of sector scanning with direct coupling is realized only to a very limited extent.

According to the present invention, the problem is solved in that ultrasonic transmitter and receiver elements are arranged in bent or curved formation in a housing containing a coupling medium which is a good conductor for the ultrasonic energy, for example water, the arrangement of the transducer elements being such that during chronologically successive excitation, the transducers direct ultrasonic beam energy through an ultrasonic window in the housing for convergence at a point outside of the housing, which point is common to all beam path directions.

In the ultrasonic applicator as specified by the invention, the target point may be shifted to varying locations outside of the housing according to the selection of the distance between the transmitter/receiver elements and the ultrasonic window in the applicator housing, and with a corresponding curvature of the ultrasonic transmitter/receiver formation, the point of convergence (serving as origin for the desired sector scanning field) may be shifted to any selected location within the body. Thus, the sector scanning procedure may also be applied with good success in the case of deeply-located acoustical bone openings. The arbitrarily selectable shifting of the intersection point, however, also makes possible the introduction of a precursory acoustic path in the coupling medium between the ultrasonic transmitting/receiving system and the body surface. If this precursory path is maintained acoustically only slightly longer than the maximum penetration depth of the ultrasonic energy in the body, multiple echos between the sound head and the body tissue are then suppressed to a great extent in a known manner. In addition, there is also no dead zone, and the ambiguities due to minor lobes are reduced to a minimum.

According to further advantageous features of the invention, means are provided for changing the curvature of the transmitter/receiver formation so as to change the target point location within the body under examination, and further to change the angle between the scanning lines where they diverge from the target point to define the sector scanning field. This adjustment of the location of the origin point for the diverging scanning lines may thus be effected without an appreciable change in the length of the precursory coupling path between the transducer system and the applicator window. According to further advantageous features of the invention, adjustment means are present in order to adjust the distance between the ultrasonic transducer system and the ultrasonic window of the applicator so as to selectively adjust the position of the target point external to the applicator and to adjust the effective length of the precursory acoustic path. According to further specific features of the invention, the transducer elements are arranged in a circular arc formation with the transducer elements arranged to direct pulses of beam energy along respective beam paths which intersect at the center of curvature of the circular arc formation.

Other objects, features and advantages of the present invention will be apparent from the following detailed description taken in connection with the accompanying sheet of drawing.

DETAILED DESCRIPTION

Figure 1:
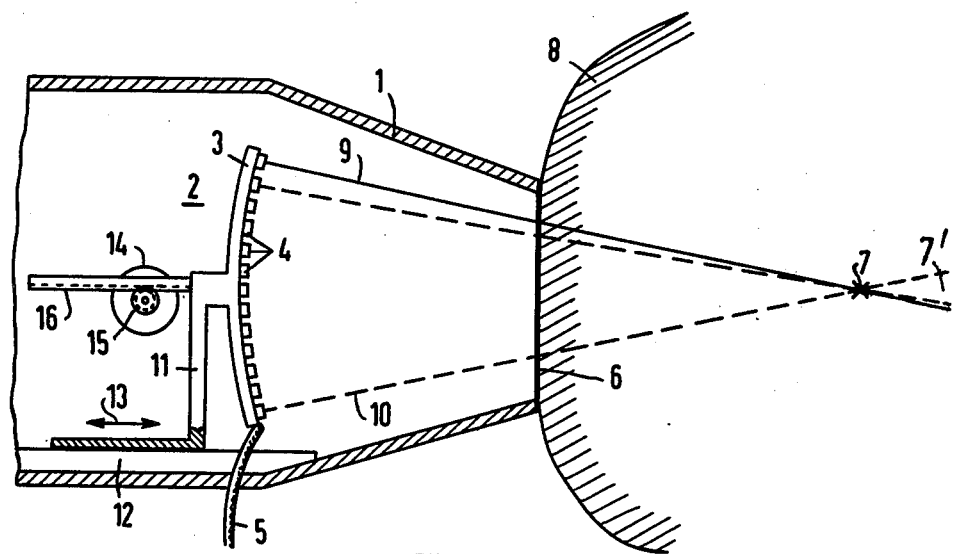
FIG. 1 illustrates the basic construction of an embodiment of ultrasonic applicator according to the present invention and comprises a partial diagrammatic longitudinal sectional view of the applicator in coupling relation to a body surface for purposes of medical diagnostic examination of an internal body region.
Figure 2:
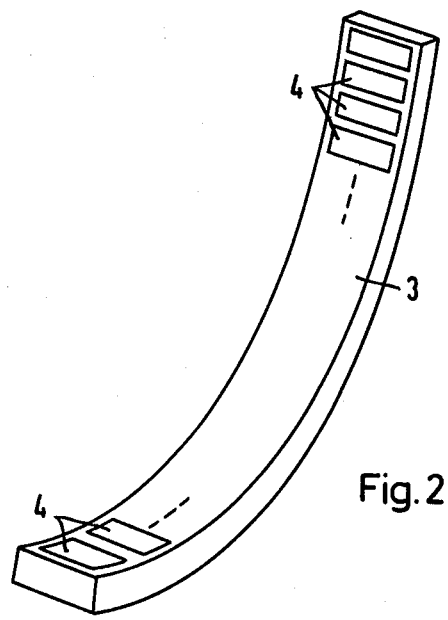
FIG. 2 is a perspective view illustrating a preferred transmitting/receiving system for the applicator of FIG. 1, and showing the arcuate formation of the transducer elements.

FIG. 1 illustrates a housing 1 of an applicator having an interior space filled with an ultrasonic coupling medium, for example degassed distilled water. An ultrasonic transmitting/receiving system is disposed in the housing and comprises a plurality of ultrasonic transducers 4 arranged in circular arc formation on a carrier strip 3 (consisting of epoxy resin provided with filler ingredients, for example). The transducer elements 4 preferably consist of barium titanate or lead zirconate. Depending upon choice, transducer elements 4 may exhibit planar radiation surfaces or, for an improved beam focusing, they may also exhibit radiation surfaces which are curved along their length dimension as viewed in FIG. 2, the length dimension of the transducer elements 4 being transverse to the longitudinal dimension of the carrier strip 3 as shown in FIG. 2. A common cable connection 5 connects the individual transducer elements 4 to an electric transmitting and receiving circuit (not shown), such circuit being coupled to an oscilloscope tube in an ultrasonic echo sectional display device for displaying echo signals received by the successive individual transducer elements 4. During chronologically successive excitation of transducer elements 4 by means of a corresponding sequential switching operation in the transmitting and receiving circuitry, the ultrasonic beam of each transducer 4 is directed through an ultrasonic window 6 (a sealing membrane which permits the ultrasonic energy to pass therethrough to the exterior of the applicator) and to a common target point 7 which is the intersection point of the ultrasonic beam paths associated with the respective transducer elements 4. The intersection point 7 is shown, for example, as being located at a selected depth within an object under examination which is indicated by reference numeral 8. Target point 7 corresponds to the center of curvature of the circular arc-shaped arrangement of transducer elements 4. Thus, point 7 is equidistant from the radiation surfaces of each of the transducer elements 4 and each of the transducer elements may direct essentially unidirectional ultrasonic energy along a beam path intersecting point 7. In FIG. 1, the ultrasonic beam path of the uppermost ultrasonic transducer 4 is indicated by reference numeral 9. The ultrasonic beam path of the lowest transducer element is designated by reference numeral 10, and is illustrated in broken lines. The beam paths 9 and 10 define the boundaries of a sector field 7', and the beam energy diverging from point 7 thus provides a scanning sector field which may be scanned by the ultrasonic beam energy from the ultrasonic transmitting/receiving system 2.

In order to shift the intersection points 7 of the ultrasonic beam paths of the individual transducer elements 4 to any selected depth in the object under examination, 8, the interval between the ultrasonic transmitting/receiving system 2 and the ultrasonic window 6 in the applicator housing 1 need only be correspondingly changed. For this purpose, for example, the ultrasonic transmitting/receiving system is secured to a supporting member 11, and the member 11 is arranged to be longitudinally slidably adjustable in the directions of the double-headed arrow 13 in a guide groove 12 at the base of the housing 1. A rotary knob 14 (indicated in dotted lines, for example), and located outside of applicator housing 1, serves the purpose of shifting the transmitting/receiving system 2, the rotary knob 14 being operable to adjust the rotational position of a pinion 15 which is engaged with the teeth of a rack 16 secured to the supporting member 11. By selecting the direction of rotational adjustment of the rotary knob 14, the transmitting/receiving system 2 can be moved toward or away from the ultrasonic window 6. The intersection point 7 of the beam paths of the transducers 4 is thereby shifted correspondingly more or less deeply below the surface of object 8. The adjustment means 11 through 16 for the ultrasonic transmitting/receiving system 2, which is manually operable, has been shown solely for the sake of example. Rotary knob 14 may, for example, be replaced by a rotary motor, for example a stepping rotary motor. By correspondingly controlling an energizing button for such a rotary stepping motor, the transmitting/receiving system 2 may be driven into a desired position at a desired longitudinal distance from the ultrasonic window 6. Changes in the acoustic path length between the transmitting/receiving system 2 and the membrane window 6, for the purpose of shifting the target point 7, however, may also be achieved, for example, by the provision of a membrane window means accommodating longitudinal adjustment of window 6 relative to the remainder of the applicator housing, while the transmitting/receiving system 2 remains fixed. For example, the fixed part of the applicator housing may terminate in an open tubular part, and this tubular part may receive in overlapping relation a closely fitting tubular part with membrane 6 at its outer end. Thus, the longitudinally adjustable membrane tube may be moved toward or away from the transducer assembly 2 while maintaining a sealing relation to the fixed part of housing 1. Such a modification of the window 6 to provide a longitudinally adjustable membrane tube, for example, is to be included as part of the present invention.

In a practical exemplary embodiment according to FIG. 2, the transmitting/receiving system 2 should preferably comprise all together approximately one-hundred (100) transducer elements 4. The individual transducer elements 4 should exhibit a width of one millimeter (1 mm) and a length of approximately five to ten millimeters (5 to 10 mm). The interval from the center of one transducer element 4 to the center of the adjacent transducer element 4 (median transducer interval) should be at a desired value in the range from approximately one to approximately one and five-tenths millimeters (1 to 1.5 mm). A value between about one-hundred millimeters (100 mm) and about one-hundred and fifty millimeters (150 mm) is recommended as the radius of curvature of the entire transducer arrangement.

It will be apparent that many modifications and variations may be effected without departing from the scope of the novel concepts of the present invention.

I claim as my invention:

1. The method of scanning internal body regions accessible through narrow acoustic apertures, which comprises:

sequentially directing ultrasonic beams from successive directions toward substantially a common point of convergence at a narrow acoustic aperture within the body such that the beams extend through the acoustic aperture and then diverge along successive scan lines forming a sector scanning configuration within an internal body region beyond the acoustic aperture, and predominantly utilizing ultrasonic echo signals produced in the sector scanning configuration beyond the point of convergence so as to predominantly provide an ultrasonic echo sectional view of the internal body region beyond such acoustic aperture.

2. The method of scanning internal body regions accessible through narrow acoustic apertures, which comprises:

sequentially directing ultrasonic beams through a body external surface from successive directions toward substantially a common point of convergence at a narrow acoustic aperture within the body and at a depth of up to several centimeters below the body external surface such that the beams extend through the acoustic aperture and then diverge along successive scan lines forming a sector scanning configuration within an internal body region beyond the acoustic aperture, and predominantly utilizing ultrasonic echo signals produced in the sector scanning configuration beyond the point of convergence so as to predominantly provide an ultrasonic echo sectional view of the internal body region beyond such acoustic aperture.

* * * * *